United States Patent [19]

Leibinsohn

[11] 4,340,051

[45] Jul. 20, 1982

[54] FINGER-PRESSURE CUSHIONING AND INDICATING DEVICE, AND SYRINGE INCLUDING SAME

[76] Inventor: Saul Leibinsohn, 11 Oley Hagardom, Rishon Lezion, Israel

[21] Appl. No.: 224,109

[22] Filed: Jan. 12, 1981

[51] Int. Cl.³ ............................................... A61M 5/00
[52] U.S. Cl. .............................. 128/215; 128/218 PA; 128/234
[58] Field of Search ................... 128/215, 216, 218 R, 128/234, 220, 218 PA, 218 P

[56] References Cited

U.S. PATENT DOCUMENTS

| | | | |
|---|---|---|---|
| 1,523,068 | 1/1925 | Hein | 128/218 R |
| 3,302,462 | 2/1967 | Pursell | 128/218 R X |
| 3,380,450 | 4/1968 | Adelberger | 128/218 R |
| 3,494,201 | 2/1970 | Roach | 128/218 R X |

FOREIGN PATENT DOCUMENTS 256696  9/1967  Austria ................................ 128/216

*Primary Examiner*—John D. Yasko
*Attorney, Agent, or Firm*—Benjamin J. Barish

[57] ABSTRACT

A device for application to a syringe, or other finger-pressure actuated article, includes a member to be received on the pressure-applying element of the article so as to be engaged by the user's finger when actuating the article, the finger-engaging member being effective to soften the pressure transmitted from the user's finger and to provide an indication to the user when a predetermined pressure has been applied. A number of embodiments are described wherein the indication of the predetermined pressure is produced by the yielding of the finger-engaging member at a greatly increased rate when the predetermined pressure is reached. Other described embodiments include a rigid element having a pointed tip engaged by the user's finger when the predetermined pressure is reached; and a still further embodiment is described wherein the indication of the predetermined pressure is provided by graduation markings.

13 Claims, 16 Drawing Figures

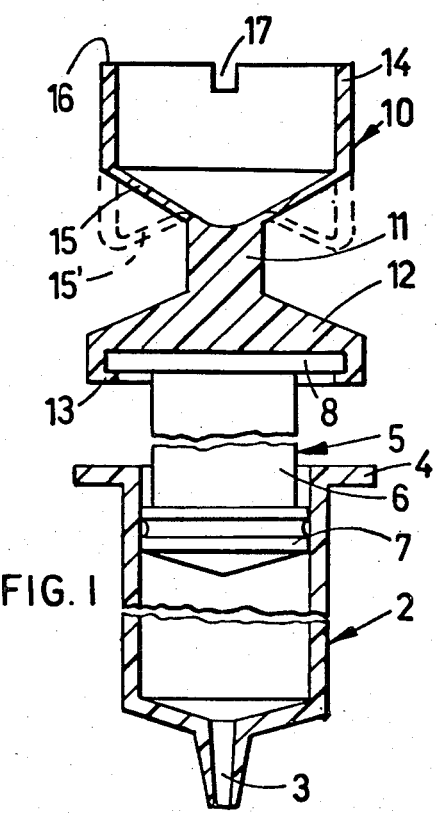
FIG. 1
FIG. 1A
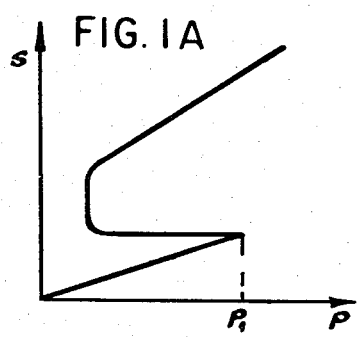
FIG. 2
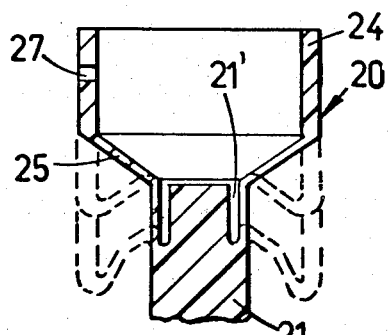
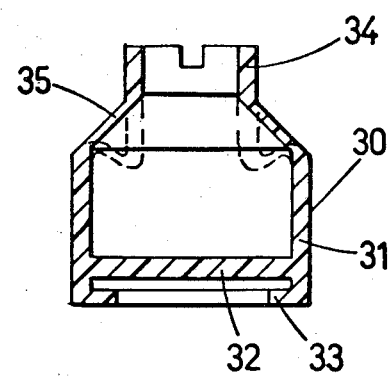
FIG. 3
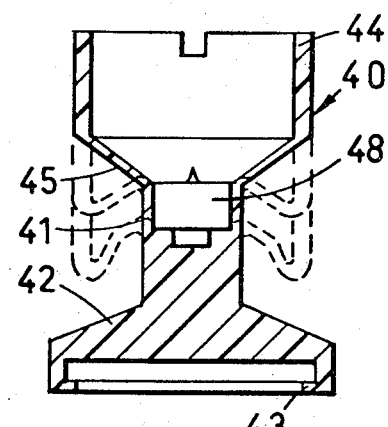
FIG. 4
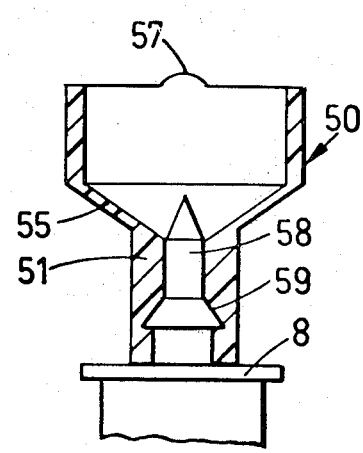
FIG. 5 ically designated 2, including a cylinder, generally

FINGER-PRESSURE CUSHIONING AND INDICATING DEVICE, AND SYRINGE INCLUDING SAME

BACKGROUND OF THE INVENTION

The present invention relates to a finger-pressure cushioning and indicating device for application to a finger-pressure actuated article. The invention is particularly useful with respect to syringes, and is therefore described below in connection with such an application, but it will be appreciated that the invention could advantageously be used in other applications as well, whenever an object is to be actuated by controlled pressure applied by a finger, hand, or the like.

Syringes commonly include a cylinder having a liquid discharge opening at one end through which the liquid contained within the cylinder is ejected, the ejection being effected by means of a plunger assembly having a piston at one end displaceable in the cylinder, and a pressure-applying element at the opposite end projecting exteriorly of the cylinder. The arrangement is such that the user holds the cylinder between two fingers and applies a third finger, namely his thumb, to the pressure-applying element of the plunger assembly, thereby to displace the piston within the cylinder and to discharge liquid through the cylinder opening.

One of the disadvantages of the known syringes, however, is that, because of the different designs, constructions and sizes of such syringes now on the market, it is very difficult, if possible at all without the use of a manometer or other pressure-measuring instrument, for the user to be aware of the pressure he is applying for injecting the liquid into the patient's body. This can be quite dangerous, since an excessively high pressure can cause rupture of the patient's vein. For this reason, many infusions are effected not by syringes, but rather by gravity-operated infusion sets, but such procedures require a considerably longer period before the fluid being injected becomes effective, which again can be detrimental to the health of the patient.

SUMMARY OF THE INVENTION

According to a broad aspect of the present invention, there is provided a yieldable finger-engaging member for application to a syringe, or other finger-pressure actuated article which includes a displaceable pressure-applying element adapted to be displaced by the user's finger when actuating same. The yieldable finger-engaging member comprises an attaching section at one end for attaching same to the displaceable pressure-applying element, a finger-engageable section at the opposite end for engagement by the user's finger, and an intermediate yielding section between the two end sections and adapted to soften the pressure transmitted from the user's finger to the displaceable pressure-applying element and to provide an indication to the user when a predetermined pressure has been applied.

A number of embodiments of the invention are described, in most of which the yieldable finger-engaging member yields at a substantially linear rate with respect to pressure until a predetermined pressure is reached, at which point it yields at a substantially greater rate, thereby providing the user with a clear indication that the predetermined pressure is reached by feeling the yielding at the substantially greater rate.

The yieldable finger-engaging member preferably includes, according to most of the described embodiments, an annular section, engageable by the user's finger, joined to a conical yielding section, the interior of these sections being vented to the atmosphere when the user applied finger pressure thereto. For example, such a yieldable member may be made inexpensively and in volume as a single unit of elastromeric material, e.g. natural or synthetic rubber.

According to another feature included in some of the described embodiments, the yieldable finger-engaging member further includes a rigid element located within the annular section so as to be engaged by the user's finger when the conical section has yielded a predetermined amount, indicating that a predetermined pressure has been applied thereto. Preferably, the rigid element has a pointed tip to be engaged by the user's finger when the predetermined pressure has been applied. Thus, this rigid element not only provides a clear feeling indication to the user that the predetermined pressure has been reached, but also applies some discomfort to him should he nevertheless continue to increase the pressure, thereby further minimizing the possibility of an excessively high pressure being unknowingly applied to the discharged liquid during its injection.

Other embodiments are described below wherein the yieldable finger-engaging member includes a first section attachable to the pressure-applying element of the syringe plunger assembly, a second section engageable by the user's finger, and a yieldable connection connecting the first and second sections. The first section may further include graduation markings to indicate the degree of displacement of the second section, and thereby the pressure applied to the second section.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a longitudinal sectional view illustrating a conventional syringe equipped with one form of yieldable finger-engaging member constructed in accordance with the present invention.

FIG. 1a is a diagram illustrating the displacement of the plunger assembly in response to a pressure as determined by the yielding characteristics of the yieldable finger-engaging member applied to the plunger assembly;

FIGS. 2–8 are fragmentary views illustrating other forms of yieldable finger-engaging members constructed in accordance with the invention;

DESCRIPTION OF PREFERRED EMBODIMENTS

Figure 6:
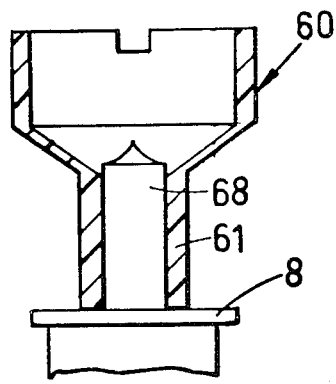

With reference first to FIG. 1, there is illustrated a conventional syringe including a cylinder, generally designated 2, formed with a liquid discharge opening 3 at one end and with finger-engaging lugs 4 at the opposite end; and a plunger assembly, generally designated 5, including a stem 6 carrying a piston 7 at one end and a pressure-applying element or disc 8 at the opposite end. As known, the user holds the cylinder 2 between two fingers engaging the lugs 4, and presses his thumb against disc 8 to displace piston 7 within the cylinder, and thereby to discharge liquid through discharge opening 3.

As noted earlier, there is a danger, particularly because of the many different designs, constructions and sizes of syringes, that the user may unknowingly apply an excessively high pressure to the liquid within the cylinder as it is discharged from opening 3, which could result in the rupture of a vein.

In order to minimize this possibility, the syringe illustrated in FIG. 1 further includes a yieldable finger-engaging member, generally designated 10, for softening the pressure transmitted from the user's finger to the pressure-applying element 8, and for providing a clear indication to the user when a predetermined pressure has been reached.

More particularly, the yieldable finger-engaging member 10 is formed as a single integral unit of elastomeric material, e.g., natural or synthetic rubber. It comprises a stem 11 joined at one end to a solid conical base 12 whose outer face is formed with an annular lip 13 for receiving the end disc 8 of the plunger assembly 5. The opposite end of stem 11 is joined to a hollow annular section 14 by a hollow conical section 15.

In use, member 10 is applied to the outer disc 8 of the syringe plunger assembly 5, so that the user, instead of applying his finger (i.e. thumb) to disc 8, now applies it to the outer face 16 of the hollow section 14 of the member. The latter outer face is preferably uneven, as shown by the provision of one or more slots 17, so that the user's finger does not seal the end of section 14, but rather permits air therein to be vented to the atmosphere as he applies pressure to this section.

It will be seen that as the user first applies pressure to the outer face 16 of the annular yieldable section 14, the wall of conical section 15 will yield at a substantially linear rate with respect to the pressure applied. Piston 7 of the plunger assembly 5 will accordingly be displaced at a substantially linear rate with respect to the pressure applied by the user, as shown in FIG. 1a.

However, when a predetermined pressure, indicated as $P_1$ in FIG. 1a, is reached, the juncture between the conical section 15 and the solid stem 11 will collapse, as shown by broken lines 15' in FIG. 1. When this occurs, member 10 will yield at a substantially greater rate, than the initial linear rate with respect to the pressure applied, as also shown in FIG. 1a, thereby providing the user with a clear feeling indicating that the predetermined pressure ($P_1$) has been reached.

It will be appreciated that the above-described yielding characteristics of member 10 may be preselected according to the length, thickness and angle of the conical section 15. Thus, irrespective of the pressure-displacement characteristics of the syringe to which member 10 is applied, the user will be provided with a clear indication of when a predetermined pressure has been applied by him to the syringe plunger assembly 5, and thereby to the liquid being discharged through the cylinder opening 3.

FIG. 2 illustrates a variation in the construction of the yieldable finger-engaging member, therein generally designated 20, to better enable the preselection of the yielding characteristics of this member. Thus, in the variation of FIG. 2, the upper end of the stem 21 is formed with an annular recess 21' at its juncture with the hollow conical section 25 connecting the stem 21 with the hollow annular section 24. The yielding characteristics of member 20 may therefore be controlled by also selecting the depth of the annular recess 21'.

FIG. 2 illustrates a further variation in that the interior of element 24 is vented to the atmosphere not by slots (17 in FIG. 1), but rather by openings 27 formed through the wall of the hollow cylindrical section 24.

FIG. 3 illustrates another construction of a yieldable member, generally designated 30, wherein the conical juncture section 35 is tapered in the opposite direction, i.e., inwardly towards its outer end rather than outwardly as in FIG. 2. In the arrangement of FIG. 3, therefore, the outer end section 34 of this member 30, engaged by the user's finger, would be of smaller diameter than in FIGS. 1 and 2. In addition, the arrangement illustrated in FIG. 3 does not include a solid stem or a solid base, corresponding to elements 11 and 12 of FIG. 1, but rather than complete interior of the member is hollow, the bottom end wall 32 being formed with the annular lip 33 for attaching this member to the plunger assembly of the syringe.

FIG. 4 illustrates a still further embodiment generally similar to FIG. 1, in that it includes a stem 41, a solid base 42 formed with the attaching lip 43, and the hollow conical section 45 joining the stem to the annular cylindrical section 44 engaged by the user's finger when applying pressure to the syringe plunger assembly. In the arrangement of FIG. 4, however, there is further included a rigid, non-yieldable element 48 located within the yieldable section 44 so as to be engaged by the user's finger when the member has yielded to a predetermined point, by the collapse of its conical wall 45, indicating that the predetermined pressure has been reached. As shown in FIG. 4, rigid element 48 is pointed at its upper tip engaged by the user's finger, to make sure that the user becomes aware that the predetermined pressure has been reached and also to apply some discomfort to the user should he unknowingly attempt to exceed the predetermined pressure.

In FIG. 4, the rigid pointed element 48 is press-fitted into a socket formed in the stem of the yieldable finger-engaging member 40.

FIG. 5 illustrates an arrangement, generally designated 50, wherein the rigid pointed element 58 is integrally formed with the end disc 8 of the syringe plunger assembly. In the arrangement of FIG. 5, the pointed element 58 is formed with a flange 59 at its lower end, and the stem portion 51 of the yieldable member 50 is formed with a bore adapted to be received on the pointed element 58 and to be retained by its flange 59. In addition, the upper face of the member 50 is formed with a plurality (e.g. 3 or 4) of projections 57 to prevent sealing its interior by the user's finger.

FIG. 6 illustrates a modified arrangement, generally designated 60, wherein the rigid element 68, also integrally formed with the end disc 8 of the syringe plunger assembly, does not include the attaching flange 59. In this case, the stem 61 of the yieldable member 60 is received on the element 68 by a friction fit. Also, here the rigid element is not pointed but rather is rounded.

It will be appreciated that the rigid element (58 or 68) may also be attached to the end disc of the syringe plunger assembly, rather than being integrally formed therewith.

Figure 7:
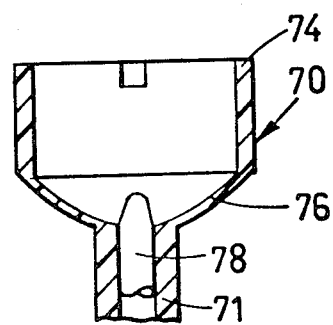

FIG. 7 illustrates a still further arrangement, generally designated 70, wherein the collapsible juncture portion, therein indicated at 76, joining the stem 71 to the finger-engaging section 74 of the yieldable member, is not of conical configuration but rather is of a curved (e.g., spherical curvature) configuration. The arrangement of FIG. 7 also illustrates the provision of the pointed rigid element 78 engageable by the user's finger when member 70 has yielded to the point indicative that the predetermined pressure has been reached.

Figure 8:
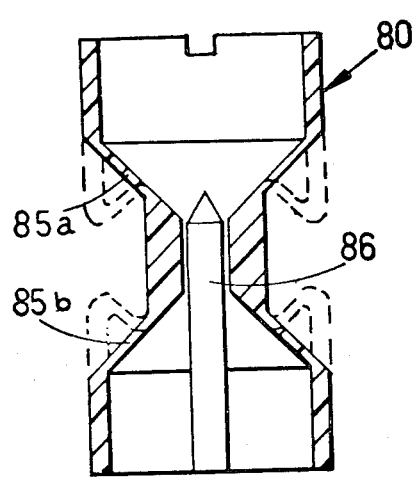

FIG. 8 illustrates a still further variation, wherein the yieldable finger-engaging member, generally designated 80, indicates to the user when two predetermined pressures have been reached. These two pressures may serve as the minimum and maximum injection pressures, respectively. For this purpose, the arrangement illustrated in FIG. 8 includes two conical juncture sections, 85a and 85b respectively, which collapse at different predetermined pressures. Thus, conical section 85a may be dimensioned so as to collapse at predetermined pressure $P_1$ in the diagram of FIG. 8a, to represent the minimum injection pressure; and conical section 85b may be dimensioned, e.g. slightly thicker, so as to collapse at the higher predetermined pressure $P_2$ representing the maximum injection pressure. The rigid pointed element 86 may therefore be located so as to engage the user's finger when he reaches or approaches the maximum pressure $P_2$.

Figure 8A:
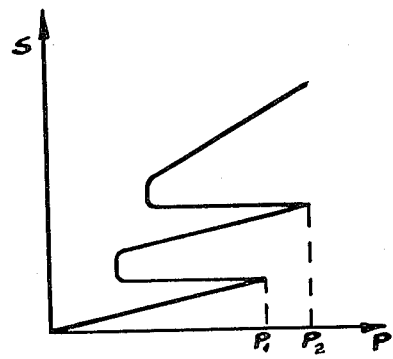
FIG. 8a is a diagram illustrating the displacement of the plunger in response to pressure in the yieldable finger-engaging member illustrated in FIG. 8.
Figure 9:
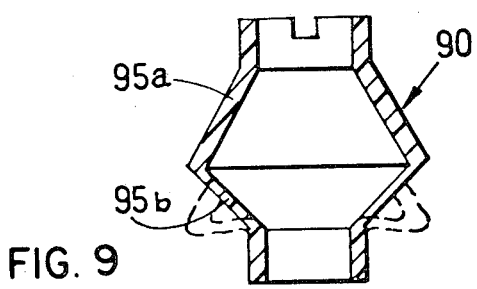
FIG. 9 illustrates a variation of the arrangement of FIG. 8.

FIG. 9 illustrates yet another variation, generally designated 80, in the two-pressure arrangement of FIGS. 8 and 8a, wherein the two collapsible conical walls, therein designated 95a and 95b, are joined to each other in the form of an accordion configuration. Again, the dimensions of these walls would be such that one (e.g. wall 95b) would collapse at a first predetermined pressure $P_1$, and the other (e.g. wall 95a) would be dimensioned so as to collapse at a higher predetermined pressure $P_2$.

In all the above-described arrangements the finger-engaging members are made of a hollow conical configuration. This is not necessary however, as other arrangements may be used.

Figure 10A:
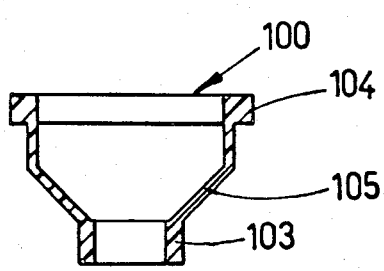
FIGS. 10a and 10b are longitudinal sectional and top plan views, respectively, of a still further embodiment of the invention.
Figure 10B:
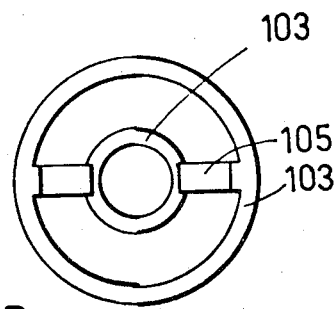

For example, FIGS. 10a and 10b illustrate an arrangement, therein generally designated 100, including an inner annular section 103 for attachment to the syringe plunger assembly, an outer annular section 104 engageable by the user's finger when applying the injection pressure, and a plurality of axially-extending, circumferentially-spaced strips 105 of elastic material connecting the two sections together. The strips 105, which may be made of elastic plastic material, are constructed according to the required dimensions and configuration so as to provide the desired pressure-displacement relationship, e.g. as illustrated in either FIG. 1a or FIG. 8a.

Figure 11C:
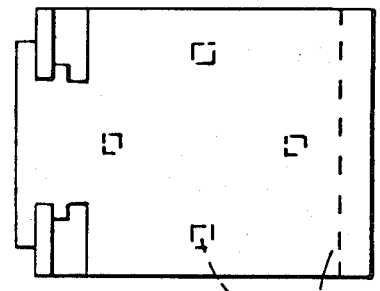
FIGS. 11a, 11b and 11c are longitudinal sectional, end elevation, and bottom plan views, respectively, of a still further embodiment of the invention.
Figure 11B:
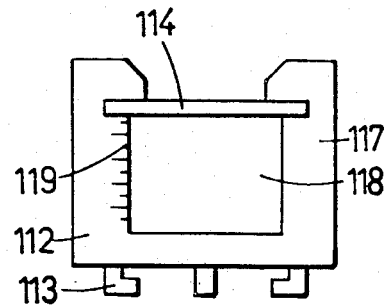
Figure 11A:
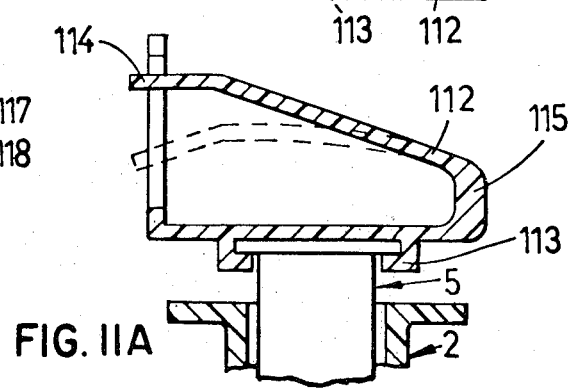

FIGS. 11a, 11b and 11c illustrate a further arrangement wherein the yieldable finger-engaging member, therein generally designated 110, is of a considerably different construction from the arrangements heretofore described in that it is made essentially of a single strip of elastic material, such as plastic. Thus, the strip of elastic material includes a base section 112 formed with lugs 113 for attaching same to the plunger assembly 5 of the syringe 2, and a finger-engaging section 114 joined to the base section 112 by a long arm 115 having a blend therein which is yieldable according to the desired pressure-displacement relationship. In this case, however, the device further includes a visual indication of the applied pressure. For this purpose, the base section 112 is formed with an end wall 117 having an opening 118 through which the finger-engaging section 114 is adapted to move when the user applies pressure to displace the syringe plunger assembly. One side of wall 117 is provided with graduation markings 119 cooperable with the finger-engaging element 114 to indicate the pressure being applied by the user.

While the invention has been described with respect to a number of embodiments, it will be appreciated that these embodiments are illustrated purely for purposes of example only, and that many other variations, modifications and applications of the invention may be made.

What is claimed is:

1. A device for application to a syringe, or other finger-pressure actuated article which includes a displaceable pressure-applying element adapted to be displaced by the user's finger when actuating same, characterized in that said device includes a yieldable finger-engaging member comprising an attaching section at one end for attaching same to the displaceable pressure-applying element, a finger-engageable section at the opposite end for engagement by the user's finger, and an intermediate yielding section between the two end sections and adapted to soften the pressure transmitted from the user's finger to the displaceable pressure-applying element and to provide an indication to the user when a predetermined pressure has been applied.

2. The device according to claim 1, in combination with a syringe including a cylinder for receiving a liquid and having a liquid discharge opening at one end, and a plunger assembly including a piston displaceable in the cylinder and further including said pressure-applying element projecting exteriorly of the cylinder to receive said yieldable finger-engaging member.

3. A device according to claim 1, wherein said yielding section of the finger-engaging member yields at a substantially linear rate with respect to pressure until a predetermined pressure is reached, at which point it yields at a substantially greater rate, thereby providing the user with a clear indication when said predetermined pressure is reached by feeling said yielding at the substantially greater rate.

4. A device according to claim 1, wherein said yielding section is of conical configuration and is vented to the atmosphere when the user applies finger pressure thereto.

5. A device according to claim 1, wherein said finger-engageable section is formed with an uneven outer annular face, which unevenness vents its interior to the atmosphere when the user applies finger pressure thereto.

6. A device according to claim 1, wherein said yieldable finger-engaging member further includes a rigid element located within said yieldable section so as to be engaged by the user's finger when the latter section has yielded a predetermined amount indicating that a predetermined pressure has been applied thereto.

7. A device according to claim 6, wherein said rigid element has a pointed tip to be engaged by the user's finger, thereby to indicate that said predetermined pressure has been applied to said yieldable finger-engaging member.

8. A device according to claim 6, wherein said rigid element is received within a socket in said yieldable finger-engaging member, the latter including an annular lip constituting said attaching section for attaching same to the pressure-applying element of the actuated article.

9. A device according to claim 6, wherein said rigid element is integrally formed on the pressure-applying element of the actuated article, said yieldable finger-engaging member being frictionally received on said rigid element.

10. A device according to claim 3, wherein said yielding section of the finger-engaging member yields at a substantially linear rate until a first predetermined pressure is reached, at which point it yields at a substantially greater rate following which it again yields at a substantially linear rate until a second predetermined pressure is reached, at which point it again yields at a substantially greater rate, thereby providing the user with a clear feeling indication of the minimum pressure represented by said first predetermined pressure, and the maximum pressure represented by said second predetermined pressure, to be applied to the pressure-applying element of the actuated article.

11. A device according to claim 1, wherein said attaching and finger-engageable sections are of annular configuration, and said yielding section includes a plurality of axially-extending, circumferentially-spaced strips of elastic material connecting together said annular sections.

12. A device according to claim 1, wherein said attaching and finger-engageable sections are integrally formed of a single strip of elastic material having a bend therein to provide said yielding section.

13. A device according to claim 1, wherein said attaching section includes graduation markings to indicate displacement of said finger-engageable section with respect thereto, and thereby the pressure applied to the latter section.

* * * * *